United States Patent [19]

Gregory et al.

[11] 4,455,532

[45] Jun. 19, 1984

[54] APPARATUS FOR MEASURING CHARGED PARTICLE BEAM

[75] Inventors: Don A. Gregory; Charles D. Stocks, both of Huntsville, Ala.

[73] Assignee: The United States of America as represented by the Administrator of the National Aeronautics and Space Administration, Washington, D.C.

[21] Appl. No.: 342,857

[22] Filed: Jan. 26, 1982

[51] Int. Cl.³ .................................. G01R 29/12
[52] U.S. Cl. .............................. 324/457; 324/71.3; 324/72.5; 250/305
[58] Field of Search ............... 324/457, 71.3, 464, 324/72.5; 250/305, 389, 397

[56] References Cited

U.S. PATENT DOCUMENTS 4,251,775 2/1981 Michel ........................... 324/72.5

FOREIGN PATENT DOCUMENTS 472425 8/1973 Australia ........................ 324/464

Primary Examiner—Micheal J. Tokar
Assistant Examiner—Kevin D. O'Shea
Attorney, Agent, or Firm—Joseph H. Beumer; John R. Manning; Leon D. Wofford, Jr.

[57] ABSTRACT

The apparatus 11 according to the present invention effectively eliminates losses to reflection and/or secondary emission of the charged particle beam 13 being measured. It comprises a sense cup (17) with an interior chamber and an entry opening (25) through which the charged particle beam (13) enters. A sense cone (19) forms the rear wall of the interior chamber with the cone apex adjacent the entry opening (25). An outer case (21) surrounds the sense cup (17) and is electrically insulated therefrom. Charged particles entering the interior chamber are trapped and are absorbed by the sense cup and cone and travel through a current measuring device (15) to ground.

6 Claims, 2 Drawing Figures

APPARATUS FOR MEASURING CHARGED PARTICLE BEAM

ORIGIN OF THE INVENTION

The invention described herein was made by employees of the United States Government and may be manufactured and used by or for the Government of the United States of America for governmental purposes without the payment of any royalties thereon or therefor.

DESCRIPTION

1. Technical Field

This invention relates to apparatus for measuring the number of charged particles per area per time, or flux, of a charged particle beam.

It is often desired to measure low and high energy charged particle beams and the present invention accomplishes that purpose without causing a large error in the measurement of the incident flux.

2. Background Art

Previously, various devices and methods have been used to measure the incident charged particle beam flux (electron, proton, etc.). Some of these devices and methods are discussed in the U.S. Pat. No. 3,239,664. There appears to be no standard to compare the effectiveness of any design and whether it was efficiently trapping the charged particles. While the prior designs depend on stopping the particle and its secondary emissions and forcing them to travel through a current measuring device to ground, it has been noticed that a large percentage of the incident beam is lost and not converted into measurable current, thereby causing a large error in the measurement of the incident flux.

DISCLOSURE OF INVENTION

The present invention has a sense cup with an interior chamber and an entry opening through which a charged particle beam enters. Within the sense cup is a cone with its base closing the rear wall and its apex adjacent to the entry opening. Charged particles entering the chamber impinged on the cone and are either absorbed or deflected to the side walls of the chamber. The arrangement effectively traps the particles even if they undergo multiple reflections so the particles will be absorbed and conducted by the metallic sense cup and metallic cone to a current meter.

The sense cup is mounted within an interior chamber of an outer case and insulated therefrom. The particles absorbed by the cone and surrounding sensing cup travel through a current meter whereby the flux can be calculated with great accuracy.

It is a principal object of the invention to provide an apparatus for measuring an incident charged particle beam flux with improved accuracy.

It is another object to provide an apparatus for effectively eliminating losses due to reflection and/or secondary emissions of the charged particle beam being measured.

DETAILED DESCRIPTION OF THE INVENTION

Figure 1:
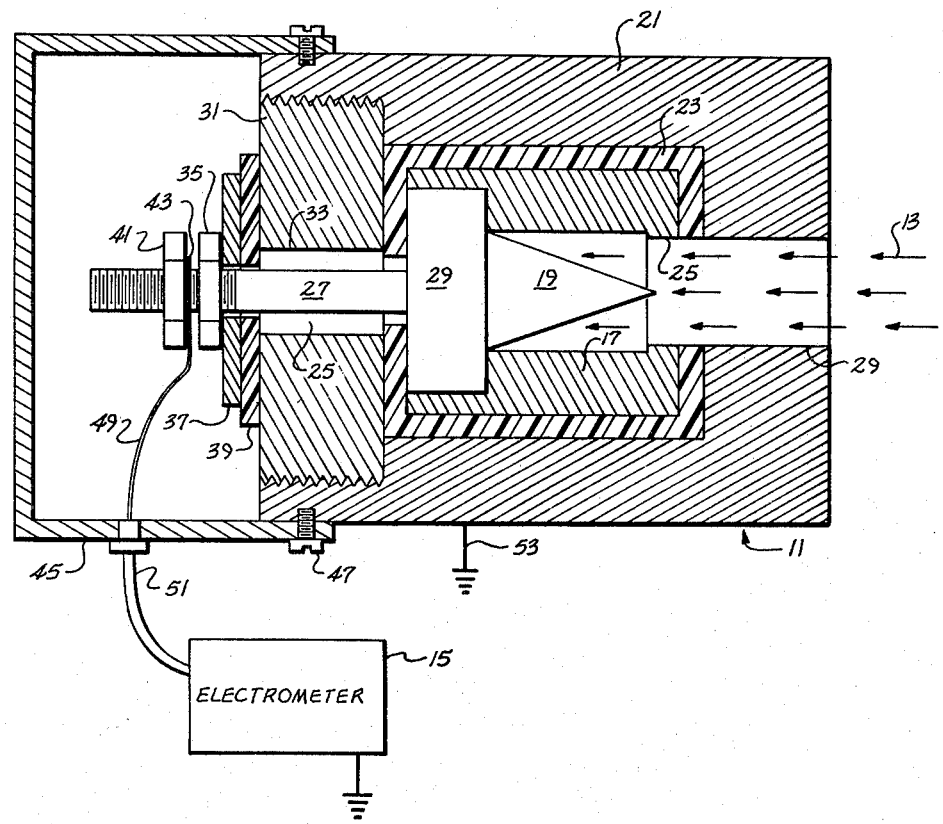
FIG. 1 is a partial sectional view of an embodiment of the invention.
Figure 2:
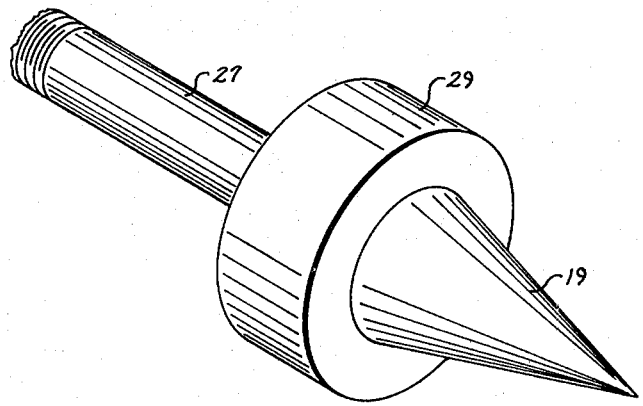
FIG. 2 is pictorial view of the forward end of the sense cone.

Referring to the drawing, FIG. 1 illustrates the apparatus 11 of the present invention which is able to trap charge particles of a beam 13 and measure them through a current measurement device 15 without significant losses due to reflection and/or secondary emission. The apparatus 11 has an inner sense cup 17 with a sense cone 19 therein supported by an outer case 21 by separated therefrom by electrical insulating material 23 and suitable air gaps 25. The sense cup 17 with its sense cone 19 and the outer case 21 are made of a metal such as aluminum. A suitable electrical insulating material is Teflon.

The sense cup 17 as illustrated is cylindrical with an interior cylindrical chamber, and a forward entry passageway 25 for the entering charged particle beam 13 to be measured. The sense cone 19 is fitted within the back passageway of the cup 17 and has its cone 19 extending forward so its apex is adjacent and near the exit of the forward passageway 25. The sense cone 19 has a shaft 27 extending rearwardly and outwardly from the sense cup 17 and the outer case 21.

The base portion 29 of the sense cone 19 is cylindrical and has a diameter smaller than the bottom or base diameter of the cone. The base portion 29 fits within a complementary opening at the rear of the cup 17. As illustrated, the bottom diameter of the cone 19 corresponds to the diameter of the interior cylindrical chamber of the cup. The interior planar angle of the cone apex is approximately 40 degrees.

The outer case 21 is similar to the sense cup 17 with an interior cylindrical chamber within which the inner sense cup 17 is fitted, and with a forward aperture passageway 29 for the charged particle beam 13 to enter. A rear threaded plug 31 closes the interior chamber whereby the interior sense cup 17 with its outer insulating material 23 is held tightly in a fixed position. The plug 31 has circular passageway 33 at its center through which the sense cone shaft 27 extends. The diameter of the passageway 33 is slightly larger than the diameter of the sense cone shaft 27, so an air gap 25 of about 0.12 inches is formed to electrically isolate the sense cone from the outer case.

The distal end portion of the sense cone shaft 27 is threaded, and a nut 35 is screwed thereon together with a metal washer 37 and insulating washer 39 of Teflon to fit snugly against the outer surface of the plug closure 31. Another nut 41 is also screwed onto the sense cone shaft 27 to clamp a washer-like electrical lead 43 between the two nuts.

A protective metallic cup 45 of aluminum or other metallic material is fitted over the rear of the outer case 21 and held there by screws 47 to shield against stray radiation. An electrical conductor 49 suitably insulated extends from the electrical lead 43 on the sense cone shaft 27 through a shielded cable 51 to a standard current measurement device 15 such as Keithley Model 610 BR Electrometer. The cable 51 should be shielded by multiple layers of metallic braiding or for superior performance by placing it inside a flexible metal tubing which has been grounded.

The outer case 21 should be grounded by being mounted on a support which is grounded or having an electrical wire 53 fastened thereto to ground. Otherwise, a charge buildup will occur in the insulation dividers 23 used which will periodically discharge and cause inaccurate readings. The outer case 21 also serves as a shield against incident radiation reaching the sense cup and cone except through the entry aperture or passageway.

We claim:

1. An apparatus for measuring incident charge particle beam flux, comprising:

a sense cup adapted to absorb and conduct incident charge particles of the beam flux;

said sense cup having a cylindrical interior chamber with a closed bottom and a front entry passageway for said charged particle beam to enter the interior chamber;

said sense cup having a sense cone forming the bottom of the interior chamber which is opposite the entry passageway and extending forward with its cone apex toward and adjacent said entry passageway, the bottom diameter of the sense cone corresponding to the diameter of the interior cylindrical chamber so the cone forms the entire bottom surface of the interior chamber, said sense cup and cone contacting each other so as to conduct therebetween the absorbed charged particles from said incident charge particle beam flux;

an electrical current measuring means for measuring the absorbed charged particles of said sense cup and said sense cone;

an outer case with an interior chamber;

said sense cup fitted within the interior chamber of said outer case;

said outer case having an entry passageway for the charged particle beam to be measured which entry passageway is axially aligned with the entry passageway of said sense cup; and electrical insulation between said outer case and said sense cup.

2. An apparatus according to claim 1, wherein:

said sense cone is fitted to the bottom of said sense cup by an integral cylindrical base portion having a diameter greater than the bottom diameter of the cone so as to have contact with the cylindrical side wall of said sense cup and forming a part of the bottom well of said sense cup;

said base portion having a shaft extending rearwardly;

said outer case having a bore in its real wall through which said shaft extends rearwardly;

said shaft having a smaller diameter than said bore in said outer case whereby an insulating air gap is formed;

insulating means for clamping said shaft relative to said outer case; and said electrical current measuring means includes an electrical conductor secured to said shaft.

3. An apparatus according to claim 1 wherein said outer case is electrically grounded to prevent an electrical charge buildup in said electrical insulator.

4. An apparatus according to claim 1 wherein said cone has an interior planar apex angle of approximately 40 degrees.

5. An apparatus according to claim 2 including a protective metallic cup secured to the rear of said outer case to shield the shaft from radiation.

6. An apparatus according to claim 5 including cable means to shield said electrical conductor from radiation.

* * * * *